(12) United States Patent
Kanner et al.

(10) Patent No.: US 9,770,263 B2
(45) Date of Patent: Sep. 26, 2017

(54) ARTIFICIAL INSEMINATION AND VAGINAL INSERTION

(71) Applicant: The Stork Ib2C, Inc., Monroeville, PA (US)

(72) Inventors: Glenn Kanner, Duxbury, MA (US); Stephen August Bollinger, Mansfield, MA (US); Edward Cruz, Newbury Park, CA (US); David Weir, Camarillo, CA (US)

(73) Assignee: The Stork Ib2C, Inc., Monroeville, PA (US)

( * ) Notice: Subject to any disclaimer, the term of this patent is extended or adjusted under 35 U.S.C. 154(b) by 306 days.

(21) Appl. No.: 14/420,447

(22) PCT Filed: Mar. 15, 2013

(86) PCT No.: PCT/US2013/032233
§ 371 (c)(1),
(2) Date: Feb. 9, 2015

(87) PCT Pub. No.: WO2014/025404
PCT Pub. Date: Feb. 13, 2014

(65) Prior Publication Data
US 2015/0196324 A1    Jul. 16, 2015

Related U.S. Application Data

(60) Provisional application No. 61/681,430, filed on Aug. 9, 2012.

(51) Int. Cl.
*A61B 17/43* (2006.01)
*A61M 31/00* (2006.01)

(52) U.S. Cl.
CPC ............ *A61B 17/43* (2013.01); *A61M 31/00* (2013.01)

(58) Field of Classification Search
CPC .............................. A61M 31/00; A61B 17/43
USPC ...................................................... 600/33–35
See application file for complete search history.

(56) References Cited

U.S. PATENT DOCUMENTS

| | | | | |
|---|---|---|---|---|
| 2,764,975 A * | 10/1956 | Greenberg | ............ | A61B 17/43 128/841 |
| 2,818,856 A * | 1/1958 | Kohl | ........................ | A61F 6/12 128/838 |
| 3,037,508 A * | 6/1962 | Friedman | ............... | A61B 17/43 128/844 |
| 5,295,984 A * | 3/1994 | Contente | ............. | A61K 9/0036 604/317 |
| 5,536,243 A * | 7/1996 | Jeyendran | ............ | A61D 19/027 600/35 |
| 6,264,638 B1 * | 7/2001 | Contente | ............. | A61K 9/0036 128/832 |
| 6,526,980 B1 * | 3/2003 | Tracy | ........................ | A61F 6/08 128/830 |
| 6,796,973 B1 * | 9/2004 | Contente | ............. | A61K 9/0036 128/832 |
| 2003/0153864 A1 * | 8/2003 | Chaffringeon | ...... | A61M 31/002 604/15 |
| 2007/0031895 A1 * | 2/2007 | Herr | ................... | A61B 10/0058 435/7.2 |

(Continued)

*Primary Examiner* — Navin Natnithithadha
*Assistant Examiner* — Sunita Reddy
(74) *Attorney, Agent, or Firm* — Foley Hoag LLP (57) ABSTRACT

Devices and methods for vaginal insertion are disclosed.

32 Claims, 14 Drawing Sheets (56) References Cited

U.S. PATENT DOCUMENTS

2008/0125692 A1\* 5/2008 Feemster ................. A61F 6/08
604/15
2011/0152606 A1\* 6/2011 Bollinger ............... A61B 17/43
600/35

\* cited by examiner

ARTIFICIAL INSEMINATION AND VAGINAL INSERTION

CROSS-REFERENCE TO RELATED APPLICATION

This application claims priority to U.S. Provisional Patent Application 61/681,430 filed Aug. 9, 2012, which is hereby incorporated herein by reference in its entirety.

SUMMARY

Devices and methods for vaginal insertion are disclosed.

DETAILED DESCRIPTION

Systems and methods for transferring and storing semen are disclosed. Such a system for semen transfer typically includes two devices: a transfer device, and an inserter. The transfer device transfers semen from an initial carrier (such as a condom) to the inserter, which is then inserted vaginally to deliver semen at or near the cervix.

Figure 1:
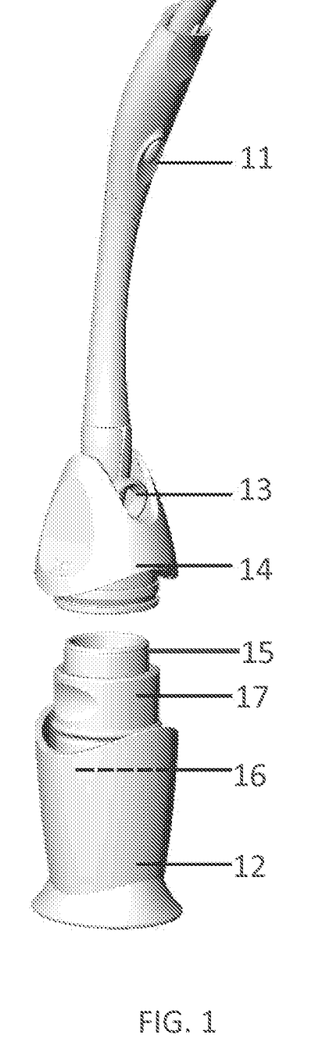
FIG. 1 schematically shows a device for vaginal insertion of a cervical cap.

FIG. 1 shows an exemplary embodiment of an inserter 11 and a transfer device 12. As will be described, the inserter 11 may interact with transfer device 12 in such a way as to cause transfer of semen in an initial carrier (such as a condom placed inside the transfer device, not shown) to the inserter 11. The inserter can be temporarily and removably attached to a cervical cap 13. A transfer top 14 is configured to mate with the transfer device that holds the semen and condom. With the inserter 11 and cap 13 attached to the transfer top 14, the inserter 11 can be lowered on to the transfer device 12 with the condom inside a carrier 17 and the distal tip of the condom in the receptacle 15. Or, as described in detail below, the cap and transfer top 14 can be lowered onto the transfer device without the inserter 11 attached. The receptacle can include an internal piston 16 (not visible, hidden inside transfer device 12), as described in detail below.

Figure 2:
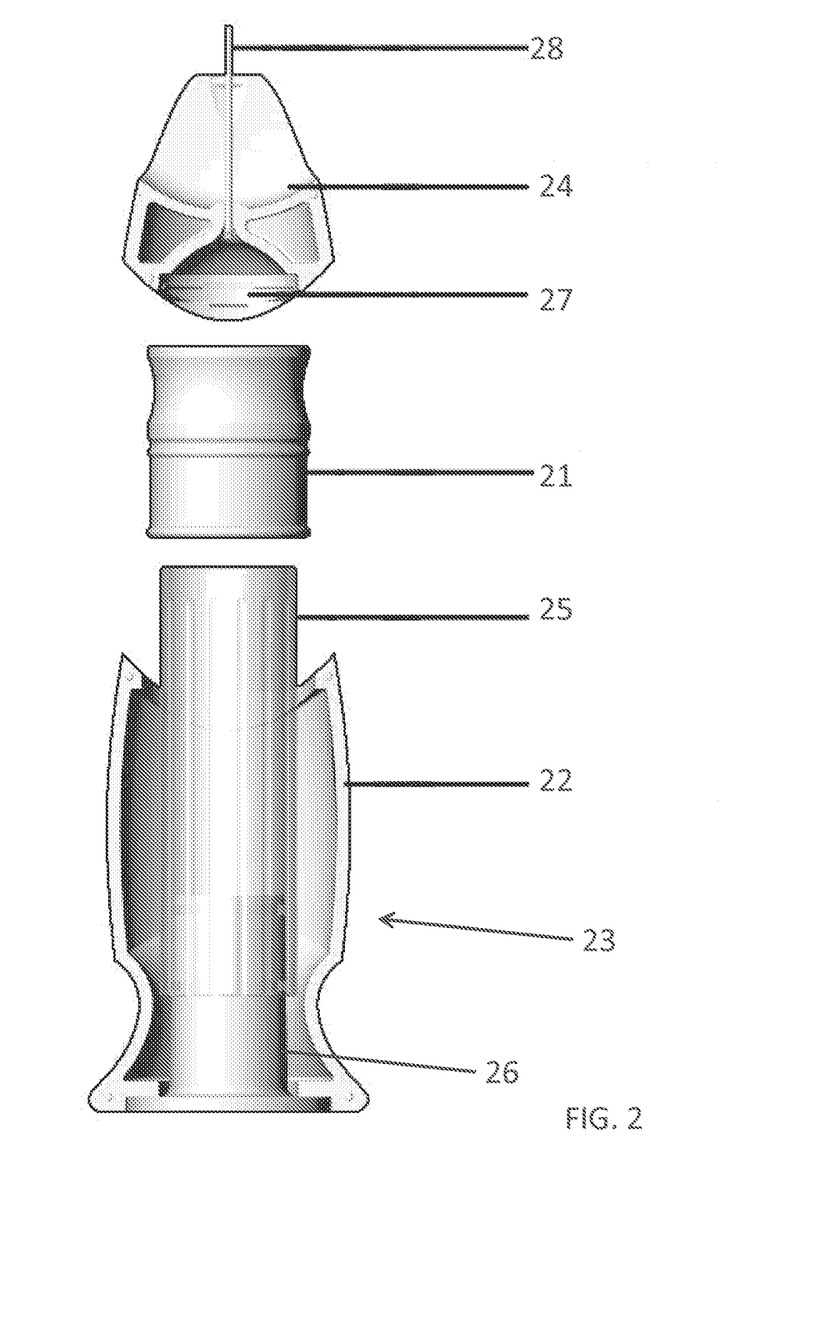
FIG. 2 schematically shows a cross-section of a portion of the device of FIG. 1.

FIG. 2 shows a cross-sectional view of one embodiment of a transfer system. A carrier 21 is attached to the open, proximal end of a condom containing semen (not shown). The carrier 21 is sized and shaped to slide along an inner tube 25 of the transfer body 23. The distal (closed) end of the condom is lowered into the inner tube 25 of a transfer body 23, after which the carrier 21 is seated at the top of the inner tube 25 trapping the wall of the condom between the two tubes 21, 25. The transfer top 24 is then placed over the transfer body 23. The transfer top 24 may be initially coupled to the insertion device (not shown), such that the insertion device handle may be used to position the transfer top 24 on the transfer body 23. The transfer top 24 is then pressed down against the carrier 21. This pressure causes the carrier 21 to slide down the inner tube 25. The condom, being attached to the carrier 21, is thereby everted over the upper lip of the inner tube 25, thereby forming a gasket-type seal between the inner tube 25 and the transfer top 24; this seal prevents loss of semen out of the transfer device and also retains air inside the cavity of the inner tube 25. As the transfer top 24 is fully seated onto the transfer body 23, the volume inside the receptacle 22, delimited by the carrier 21 and a base 26 of the receptacle (such as a piston), is decreased. This decrease in volume exerts pressure on the condom and complies the interior surface of the condom onto the inner wall of the transfer top 24. Consequently, pressure is exerted on the semen inside the condom. The semen is therefore expressed upward into a cavity 27 inside the transfer top 24 and thence through an injector 28 into a cervical cap preloaded on the inserter. The cervical cap is preloaded on the inserter by, for example, jaws that squeeze the cervical cap closed. Initially, the injector 28 is interposed within the flexible material of the cervical cap, preserving a seal between the squeezed sides of the cervical cap preventing loss of semen from the cervical cap. As the transfer top 24 is fully seated on the transfer body 23 and the semen transfer is accomplished, the inserter, with attached cervical cap, is released from the transfer top 24. The inserter can then be inserted vaginally, cervical cap first; the cervical cap itself provides a soft leading edge for safety and comfort. A latch, lever, button, or other mechanism in the inserter allows the user to open the cervical cap, effectuate semen release, then release the cervical cap, or at least to open the jaws to permit semen presentation. The device may then be withdrawn after a delay suitable to permit migration of sperm out of the semen in the cervical cap and through the os of the cervix. Alternatively, the device may be withdrawn immediately but the cervical cap left behind, optionally with a removal-string attached for retrieval. A removal-string may be attached to the cap at one end of the string with a user-end of the string designed to protrude from the vagina. The user-end of the removal string may be affixed to itself so as to form a loop. The user end of the string might also be attached to a pull-tab, button or other device designed to allow the user to more easily pull on the string. Alternatively, the string may be attached to the cap at both ends so as to form a loop, with the loop designed to protrude from the vagina. All the above removal string configurations can be applied to any object inserted into the vaginal tract that a user may later wish to remove.

Figure 3:
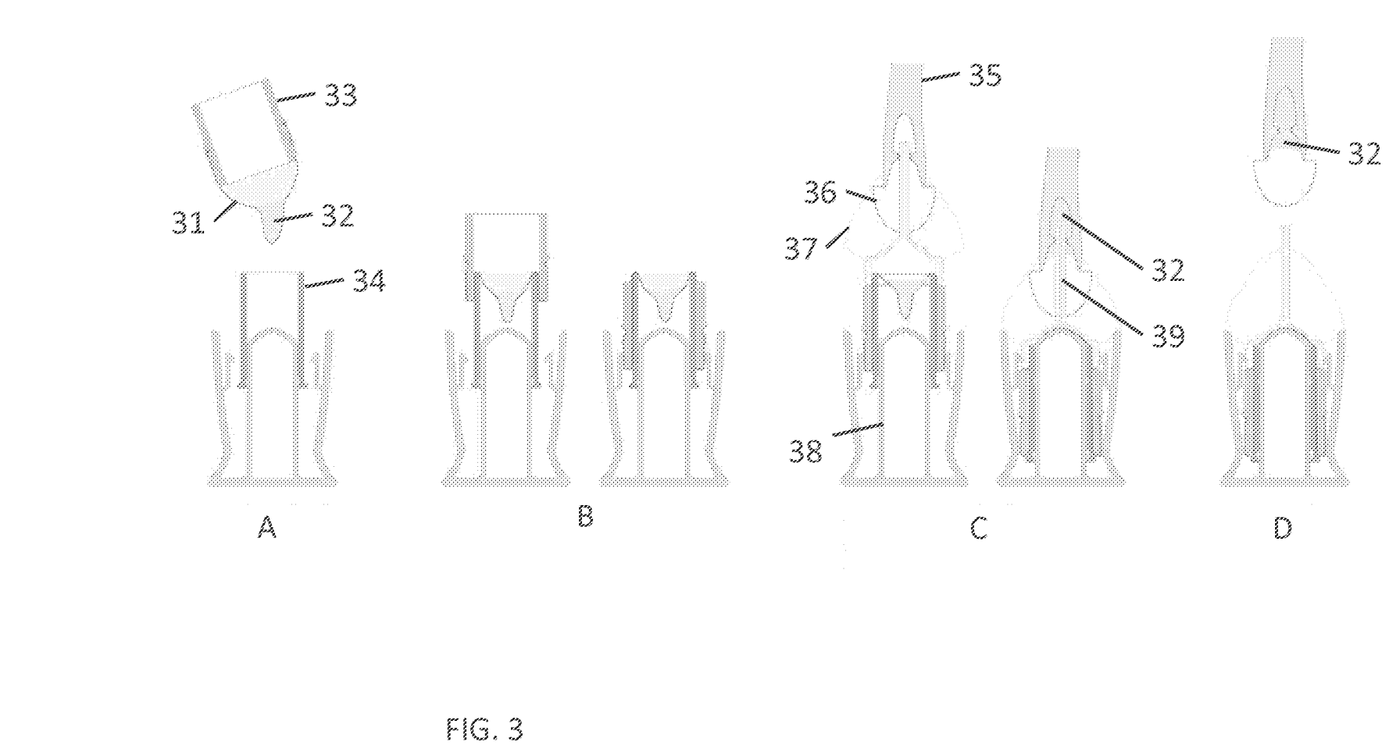
FIG. 3 schematically shows a method of using the device of FIG. 1 in cross-section.

FIG. 3 shows a cross-sectional view of another embodiment. In step A, a condom 31 containing semen 32 is fitted to the end of a carrier 33. In step B, the carrier 33 is lowered on to a receptacle 34. The carrier 33 is lowered around receptacle 34 so that the top of the carrier is below the top of the receptacle. In step C, an insertion device 35, fitted with a cervical cap 36 and a transfer top 37, is lowered onto the receptacle 34, and pushed down until the transfer top 37 bottoms out. Piston 38 applies pressure to condom 31 forcing the semen 32 up through inserter 39 to the reservoir of the cervical cap 36. Insertion device 35 is then lifted off of the transfer top 37 with the cervical cap 36 charged with semen 32 and ready for use.

Rather than placing the inserter on the transfer body, a sealing cap may instead be placed; this transforms the transfer device into a storage capsule for later use.

Although described herein with respect to cervical caps used in artificial insemination, a transfer system can be used to position an object other than a cervical cap in the vaginal tract, for instance a diaphragm, pessary, tampon, suppository, pH monitor, or other contraceptive or other vaginal devices. The same transfer system can of course be used to position cervical caps for purposes other than artificial insemination, for example contraception.

Example 1

1. The condom is used as a standard condom, receiving semen in the closed distal end, and is retrieved for transfer.

Figure 4:
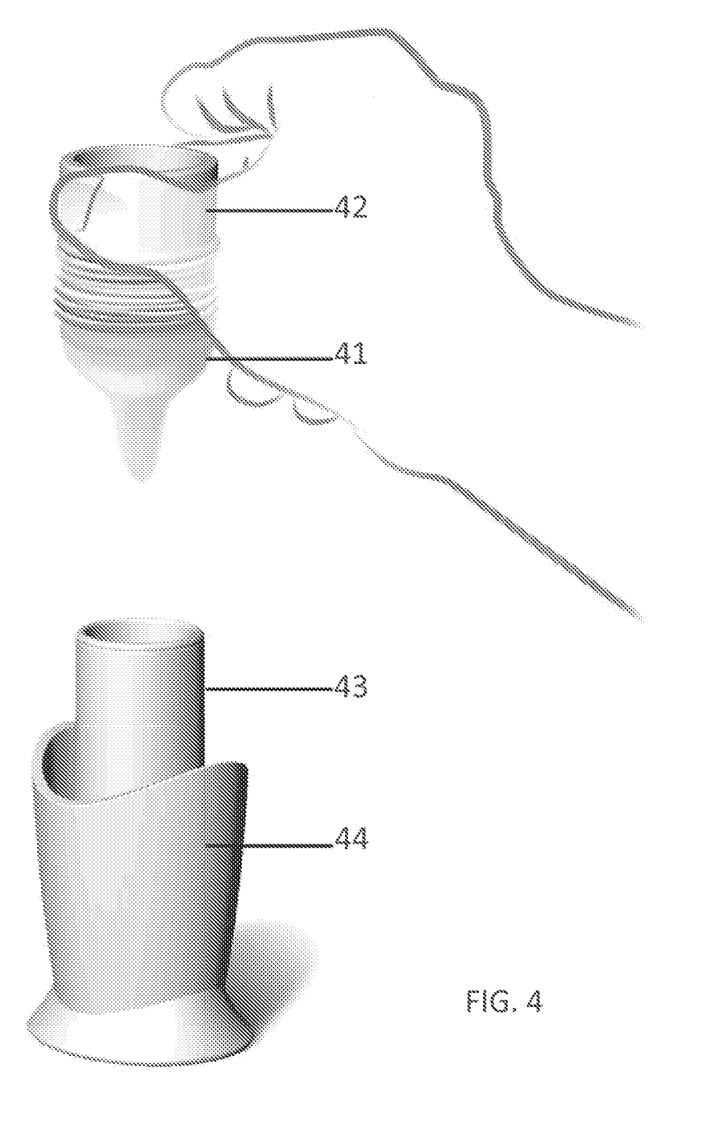
FIGS. 4-9 schematically show a method of using the device of FIG. 1.

2. A user fits the open, proximal end of the condom 41 onto the carrier 42 using an alignment mark on the condom or carrier (FIG. 4).

Figure 5:
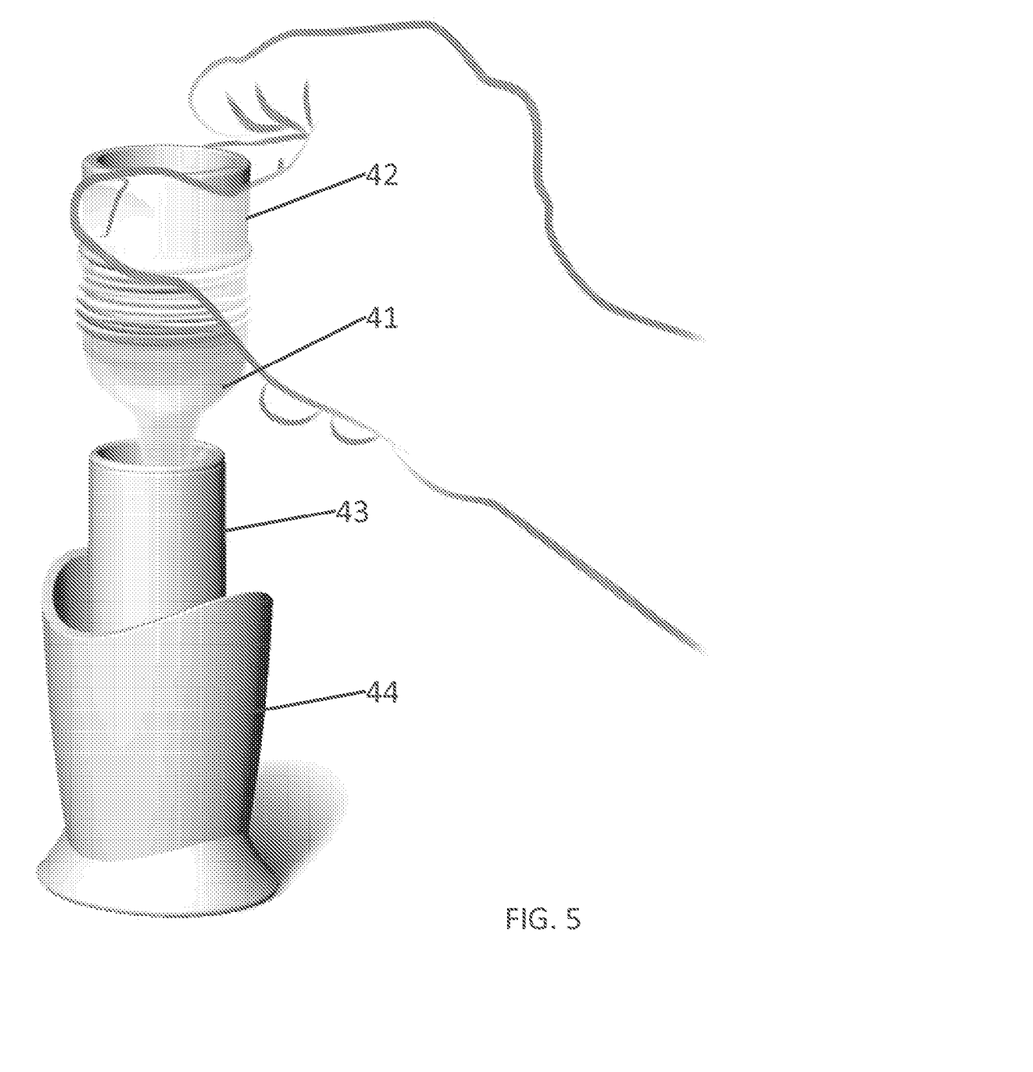

3. Holding the carrier 42, the user introduces the condom 41 into the opening of the inner tube, or receptacle 43, of the transfer body 44 and lowers the carrier (FIG. 5), fitting the carrier outside of the receptacle, until the carrier meets a stop.

Figure 6:
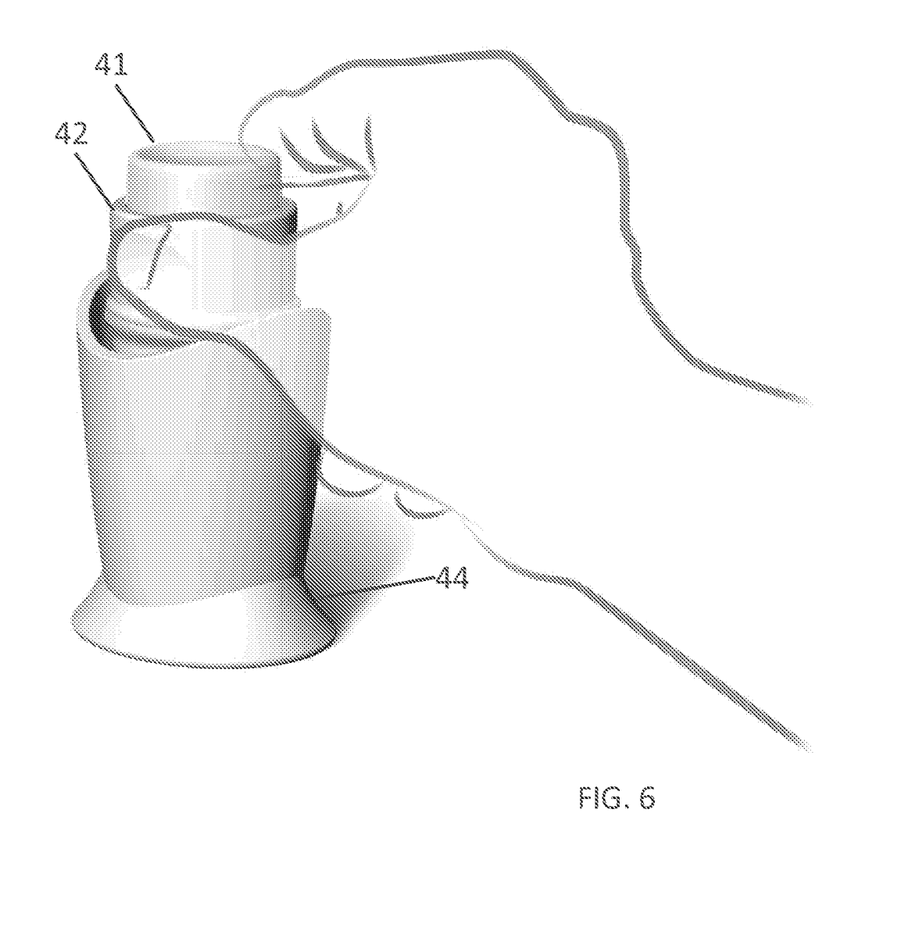

4. The carrier 42 is thus installed outside the receptacle 43 of the transfer body 44, and the semen in the closed distal end of the condom 41 is "presented" atop the receptacle 43 of the transfer body 44 (FIG. 6).

Figure 7:
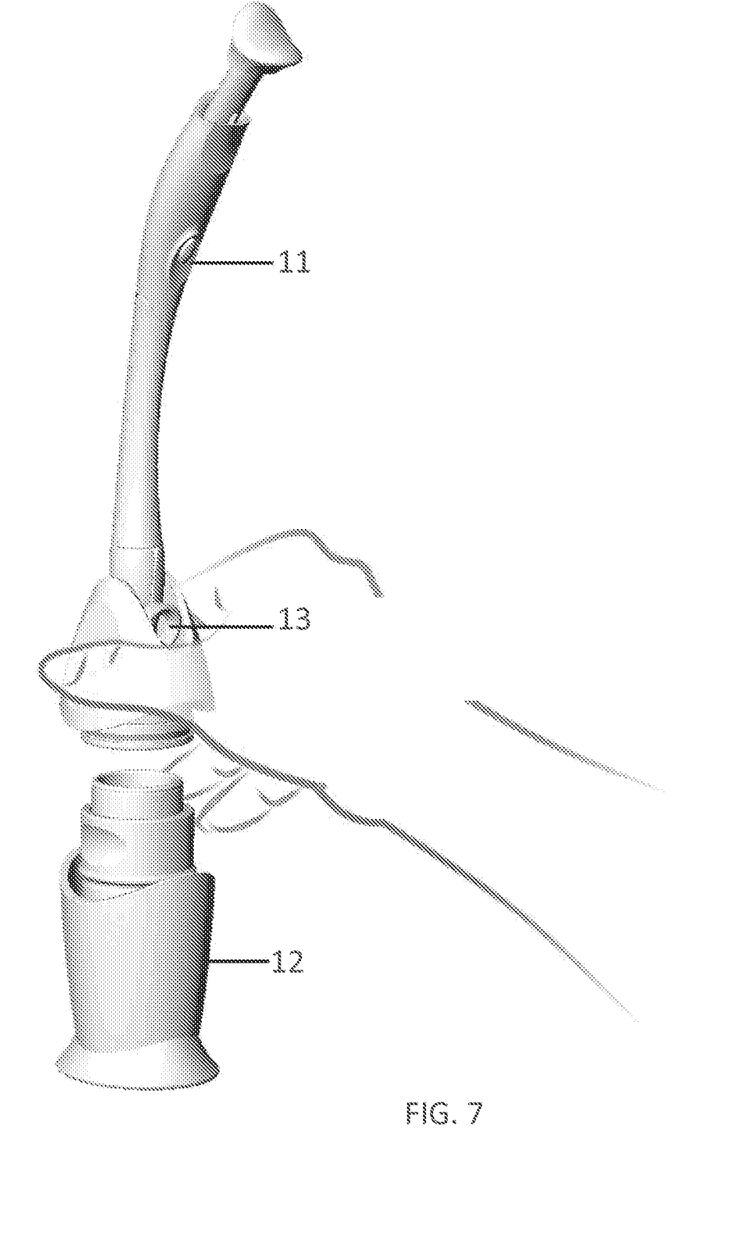
Figure 8:
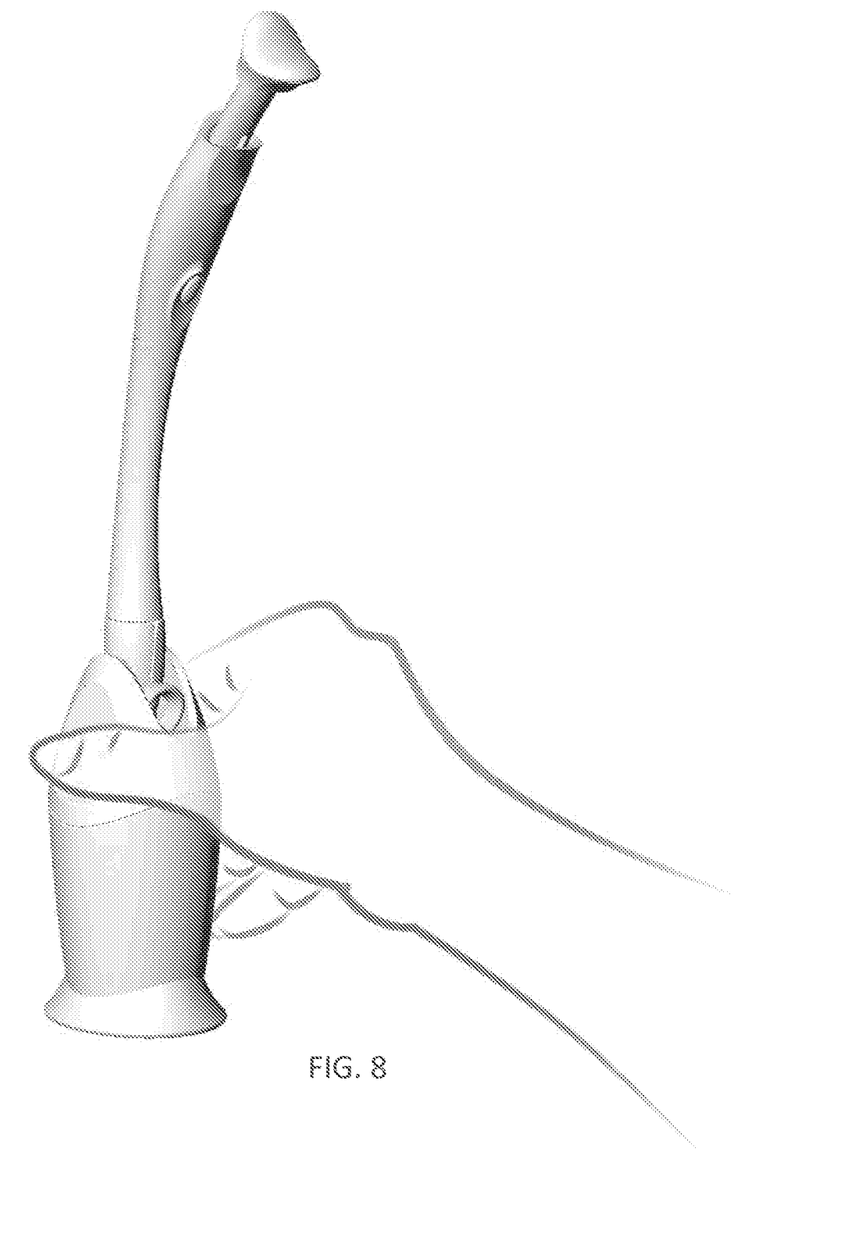

5. A user lowers the inserter 11, with its pre-loaded cervical cap 13 and transfer top, onto the transfer device (FIGS. 7-8). The downward action of the inserter and transfer top automatically performs the transfer of the semen to the pre-loaded cervical cap as follows:

A. The transfer top first seals around rim of the carrier, then slides the carrier down around the piston. This downward motion of the carrier and receptacle is equivalent to an upward motion of the piston relative to the outer and receptacles.

B. The piston thus raises the closed, distal end of the condom up, into the sealed inner cavity of the transfer top, and presses the condom fully onto the surface of the inner cavity.

C. The resultant pressure causes semen to travel up out of the transfer top through the injector (between the contacting rim surface of the cervical cap and into the cervical cap.

Figure 9:
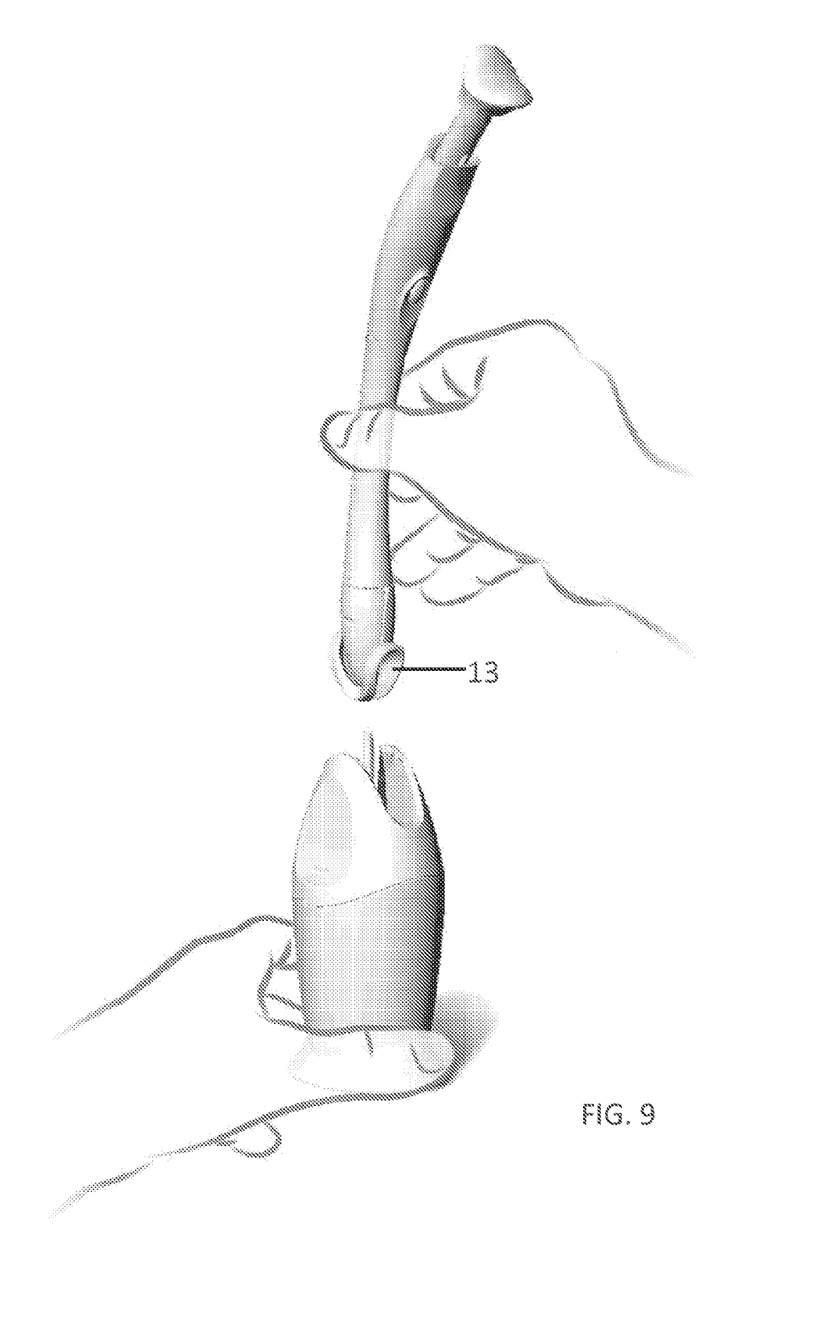

D. When the transfer top reaches the end of its downward motion, the transfer top automatically snaps into and is secured onto the transfer body. The user then pulls the Inserter 11 and cervical cap 13 (which has been loaded with the semen from the condom) out of the transfer top and off of the injector. The cervical cap rim surfaces will seal where the injector passed through and the inserter and cervical cap will be prepared to use for placement of the cervical cap (FIG. 9).

Figure 10:
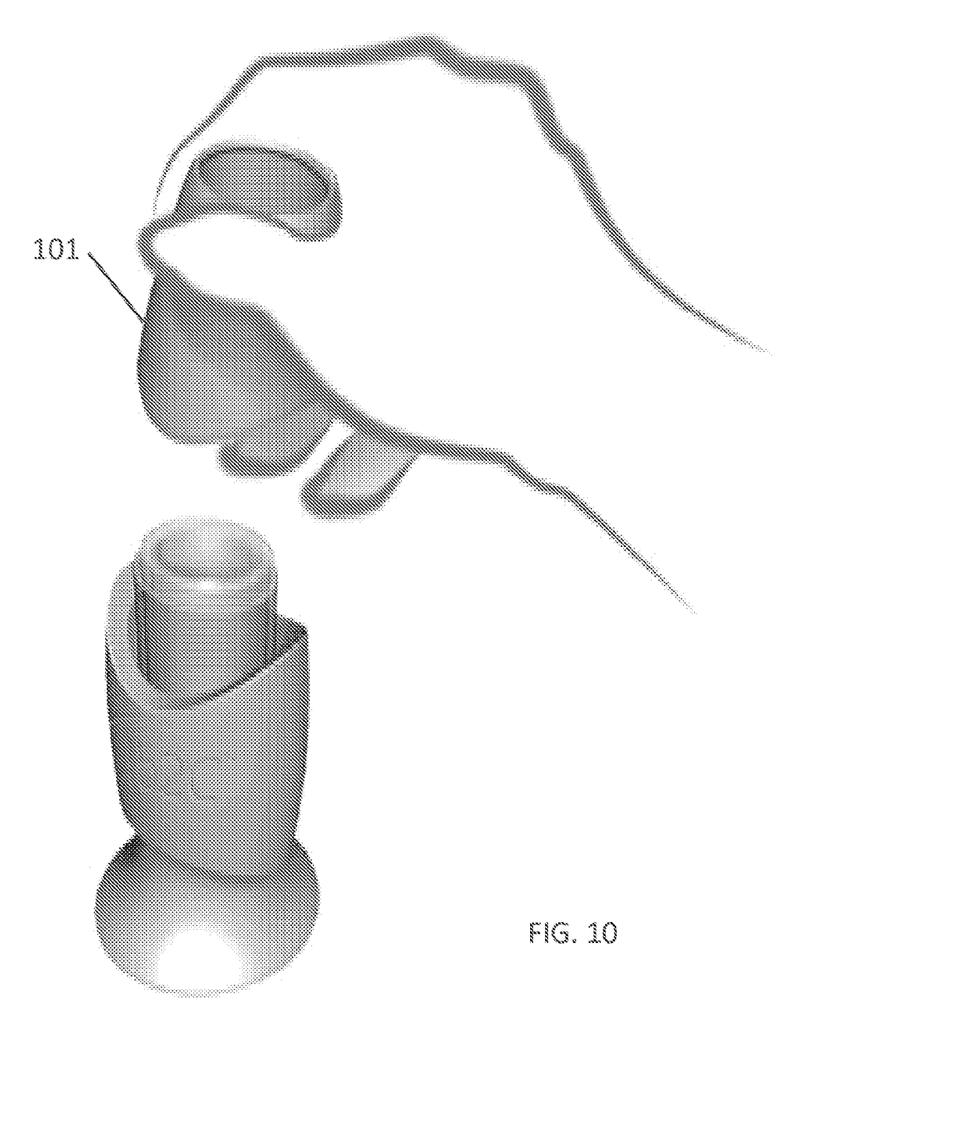
FIG. 10 schematically shows another method of using the device of FIG. 1.

Alternatively, as shown in FIG. 10, the transfer body may instead be capped 101, with the semen sealed inside for storage and future use.

Example 2

Figure 11:
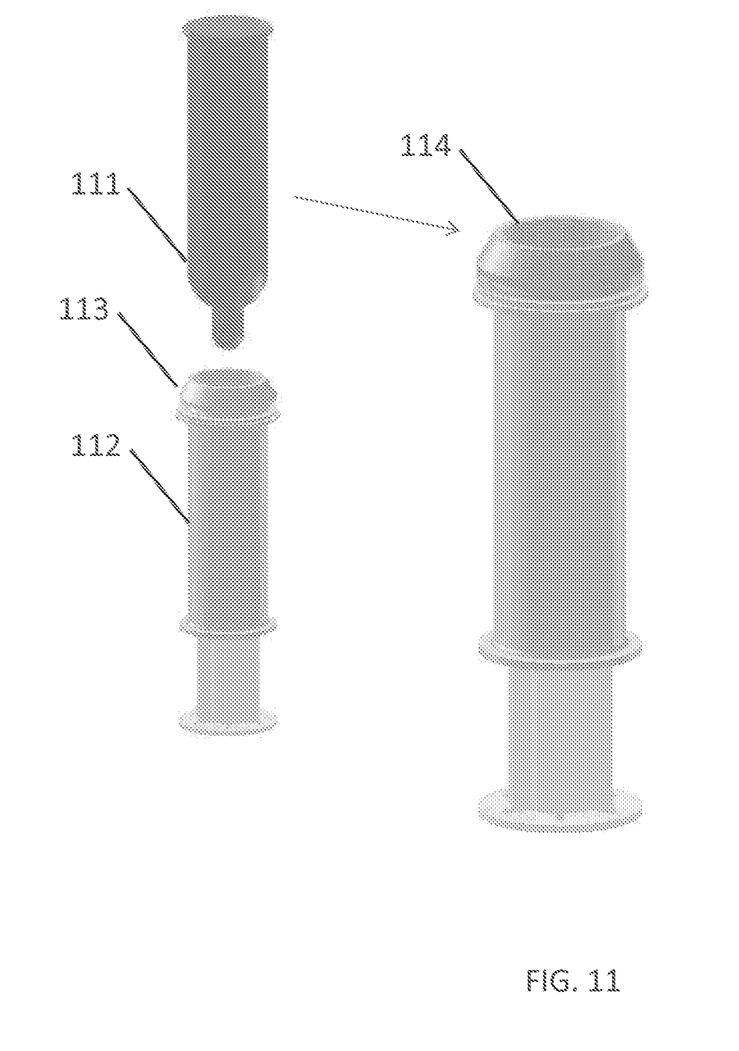
FIGS. 11-13 schematically show a method of using an alternative device for vaginal insertion of a cervical cap.
Figure 12:
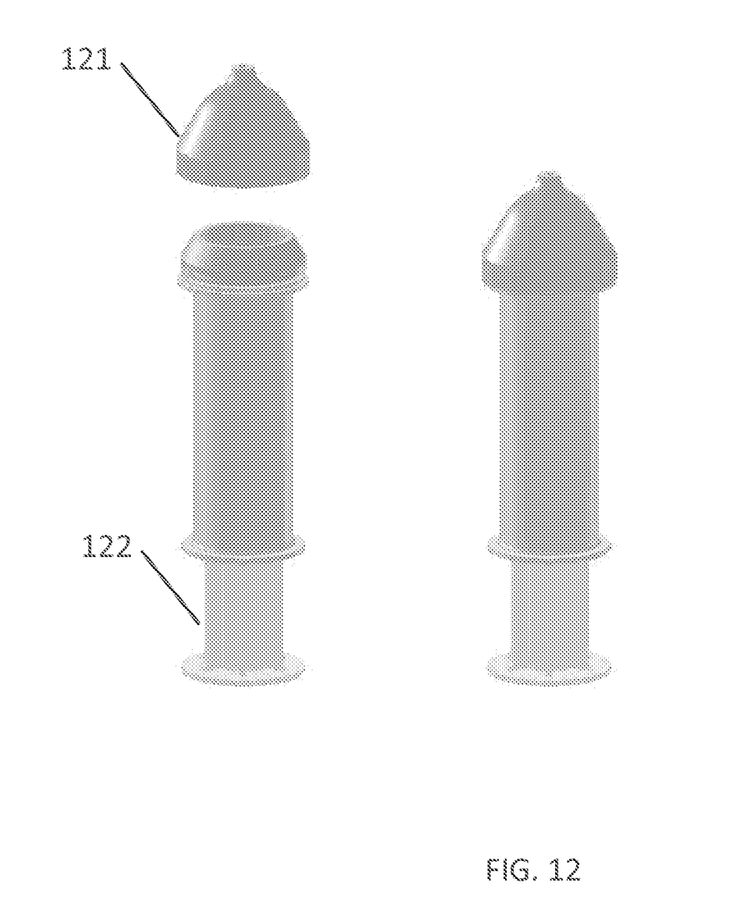
Figure 13:
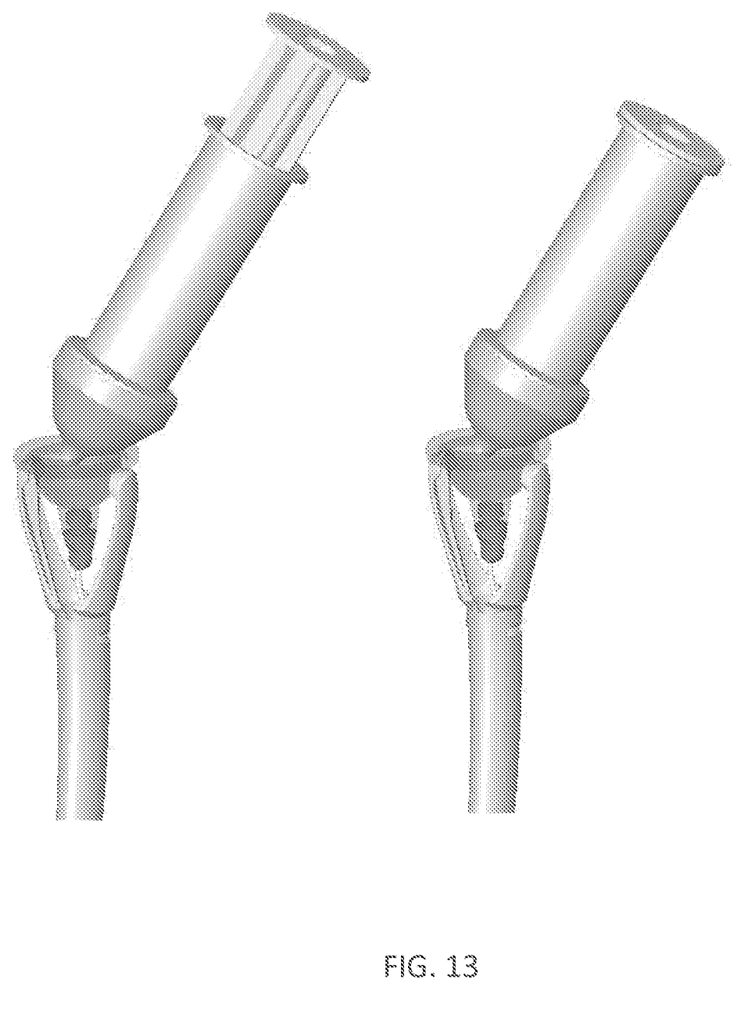

FIGS. 11-13 schematically show an alternative embodiment. A condom 111 is used as a standard condom, receiving semen in the closed distal end, and is received for transfer. As shown in FIG. 11, the condom 111 is lowered into a receptacle 112 and the proximal end 114 of the condom is everted over the outer perimeter 113 of the receptacle. In the depicted alternative embodiment, the everted proximal end of the condom may be moved axially along the outer perimeter of the receptacle so that the distal end of the condom is raised upward toward the top of the receptacle. A transfer top 121 is then placed atop the receptacle 112, as shown in FIG. 12. The condom may act as a gasket to form a substantially air-tight seal between the receptacle and the transfer top. The receptacle then defines a substantially air-tight space, where one part of the receptacle is movable as a piston 122. As shown in FIGS. 11-13, the receptacle and piston can be configured similar to a syringe's barrel and plunger respectively. As shown in FIG. 13, the receptacle, with the attached transfer top and condom, can be positioned with the transfer top adjacent to a cervical cap, in some cases by inverting the assembled transfer top, receptacle and condom. Once in place, the piston is actuated, reducing the size of the air-tight portion of the receptacle, and effecting a transfer of the semen from the distal end of the condom through a passage in the transfer top. The semen is then deposited in the cervical cap, as shown in FIG. 13. Similar to other embodiments, the inserter may seal the cervical cap closed so as to retain the semen. The inserter can then be inserted vaginally to position the cervical cap over the cervix, where the cap can be opened and the semen released so that the sperm are allowed to migrate through the cervix.

Figure 14:
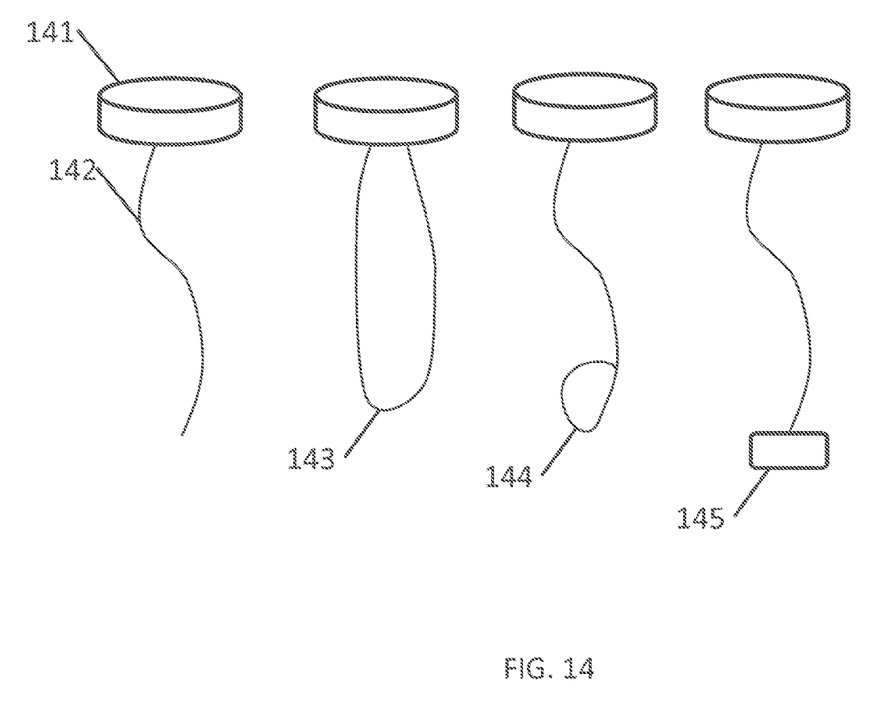
FIG. 14 schematically shows a cervical cap.

FIG. 14 schematically shows a cervical cap 141 with a removal string 142. The string 142 can be attached to the cap 141 at only one end. The string can be attached to the cap at both ends so as to make a loop 143. The end of the string can be attached to the string itself so as to form a loop 144 while only one end is attached to the cap 141. The string may be attached to the cap at one end and attached to a pull-tab, button or other device 145 designed to allow the user to more easily pull on the string.

Methods for aiding conception can include fitting a condom having a closed, distal end containing semen onto a carrier, placing the carrier atop a receptacle such that the closed, distal end of the condom is lowered into the receptacle, placing a transfer top defining a passage onto the carrier, and moving a piston relative to the receptacle causing transfer of semen from the closed, distal end of the condom through the passage into a cervical cap, wherein the receptacle is made effectively sealed from air passage by the piston at the bottom end and the transfer top and the condom at the top end, wherein the space between the transfer top and receptacle is sealed by the condom. Such methods can further include sliding the carrier axially along the outer perimeter of receptacle until the closed, distal end of the condom is raised upward towards the top of the receptacle. Such methods can include sliding the carrier axially along the outer perimeter of receptacle until the carrier meets a stop. Such methods can include pushing down axially on the receptacle with the transfer top.

In such methods, the transfer top can be removably connected to an inserter, the cervical cap can be contained within an inserter, and/or the cervical cap can be separably connected to an inserter. Such methods can include connecting the cervical cap to an inserter and/or transferring the cervical cap from the transfer top to an inserter. In such methods the carrier can be ring-shaped and the receptacle can be cylindrical.

Methods for semen transfer can include fitting a condom onto a carrier defining a passage, the condom comprising a closed distal end in which semen is located, placing the carrier in relation to a receptacle such that both the semen and the closed distal end of the condom are inside the receptacle, and moving a piston relative to the receptacle to effect a transfer of semen from the closed distal end of the condom through the passage into a cervical cap, wherein the receptacle is made effectively sealed from air passage by the piston at the receptacle's bottom end and by mating of surfaces between the receptacle and the condom at the receptacle's top end. Such methods can include sliding the carrier axially along the outer perimeter of receptacle until the end of the condom is raised upward towards the top of the receptacle, and/or until the carrier meets a stop. In such methods, transfer top can be connected to an inserter, the cap can be contained within an inserter, and/or the cap can be connected to an inserter. Such methods can also include connecting the cap to an inserter, and/or transferring the cap from the carrier to an inserter. In such methods, the carrier can be ring-shaped and the receptacle can be cylindrical, and/or the carrier can be shaped to match the receptacle shape.

Methods for transferring semen from a device can include lowering the closed, distal end of a condom containing semen ejaculate into a receptacle, everting the open, proximal end of the condom over the outer perimeter of the receptacle, placing the transfer top defining a passage atop the receptacle, and moving a piston relative to the receptacle to effect a transfer of semen ejaculate from the closed distal end of the condom through the passage in the transfer top which the semen may pass through to exit the device, wherein the receptacle is made effectively sealed from air passage by the piston at the bottom end and by the mating surface between the receptacle and the transfer top at the top end. In such methods, the open, proximal end of the condom can be moved axially along the outer perimeter of the receptacle after the condom is everted until the closed, distal end of the condom is raised upward towards the top of the receptacle before placing the transfer top. In such methods a cervical cap can be separably attached to the transfer top, the transfer top can be separably connected to an inserter, the cervical cap can be contained within an inserter, and/or the cervical cap can be separably connected to an inserter. Such methods can also include connecting the cervical cap to an inserter, and/or transferring the cervical cap from the transfer top to an inserter. In such methods can include inverting the receptacle, piston and transfer top such that the top of the device comprising the transfer top becomes the bottom of the device and the bottom of the device, comprising the receptacle and piston becomes the top of the device before transferring the semen through the passage in the transfer top. Such methods can also include placing the transfer top on the receptacle for protected storage of the semen, and/or placing a cover on the receptacle before the transfer top for protected storage of the semen.

In any method involving a cervical cap, a removal string can be attached to the cervical cap. The removal string can be of sufficient length that when the cervical cap is placed over a person's cervix at least a portion of the string may protrude from the person's vagina. The method can include inserting the cervical cap into a person's vagina such that a portion of the removal string protrudes from the vagina. The string can have two ends and both ends can be attached to the cervical cap so as to form a loop, or only one end can be attached to the cervical cap, or the string may be attached to the cervical cap at a midpoint that is at neither end. The portion of the removal string protruding from the vagina can be formed into a loop. The portion of the removal string protruding from the vagina can be affixed to a pull-tab, button or other device designed to allow the user to more easily pull on the string.

Methods for vaginal insertion of an object can include attaching an object to an insertion means for vaginal insertion and deposition, inserting the insertion means into a person's vagina, and depositing the object inside the vagina. The insertion means can include means for removably attaching the object to the insertion means, and means for releasing the object from the insertion means so as to deposit the object at a desired location. In such methods the object can be, for example, a diaphragm, a pessary, a tampon, a suppository, or a pH monitor. In such methods a removal string can be attached to the object. The removal string can be of sufficient length that when the object is placed in the vagina at least a portion of the string may protrude from the person's vagina. Such methods can include depositing the object such that at least a portion of the removal string protrudes from the vagina. The string can have two ends and both ends can be attached to the object so as to form a loop, or only one end can be attached to the object, or the string may be attached to the object at a midpoint that is at neither end. The portion of the removal string protruding from the vagina can be formed into a loop. The portion of the removal string protruding from the vagina can be affixed to a pull-tab, button or other device designed to allow the user to more easily pull on the string.

An object sized and shaped for insertion and deposition in the vaginal tract of a human can include a removal string. The removal string can have a first end and a second end. The first and second ends can both be attached to the object. The string can be of sufficient length that when the object is placed in the vaginal tract at least a portion of the string may protrude from the vagina. The object can be, for example, a diaphragm, a pessary, a tampon, a suppository, or a pH monitor.

We claim:

1. A method for aiding in conception, comprising:
    fitting a condom comprising a closed, distal end containing a semen deposit onto a carrier;
    placing the carrier atop a receptacle with the closed, distal end of the condom disposed in the receptacle;
    placing a transfer top defining a passage onto the carrier; and
    moving a piston relative to the receptacle and transferring of the semen deposit from the closed, distal end of the condom through the passage into a cervical cap;
    wherein the receptacle is effectively sealed from air passage by the piston at the bottom end and the transfer top and the condom at the top end, wherein a space between the transfer top and receptacle is sealed by the condom; and
    pushing down axially on the receptacle with the transfer top.

2. The method of claim 1, further comprising sliding the carrier axially along an outer perimeter of receptacle until the closed, distal end of the condom is raised upward towards the top of the receptacle.

3. The method of claim 1, further comprising sliding the carrier axially along an outer perimeter of receptacle until the carrier meets a stop.

4. The method of claim 1, wherein the transfer top is removably connected to an inserter.

5. The method of claim 1, wherein the cervical cap is contained within an inserter.

6. The method of claim 1, wherein the cervical cap is separably connected to an inserter.

7. The method of claim 1, comprising the step of connecting the cervical cap to an inserter.

8. The method of claim 1, comprising the step of transferring the cervical cap from the transfer top to an inserter.

9. The method of claim 1, wherein the carrier is ring-shaped and the receptacle is cylindrical.

10. A method for semen transfer, comprising:
    fitting a condom onto a carrier defining a passage, the condom comprising a closed distal end in which a semen deposit is located;

placing the carrier in relation to a receptacle with both the semen deposit and the closed distal end of the condom disposed inside the receptacle; and moving a piston relative to the receptacle and transferring the semen deposit from the closed distal end of the condom through the passage into a cervical cap, wherein the receptacle is effectively sealed from air passage by the piston at the receptacle's bottom end and by mating of surfaces between the receptacle and the condom at the receptacle's top end; and sliding the carrier axially along an outer perimeter of receptacle until the end of the condom is raised upward towards the top of the receptacle.

11. The method of claim 10, further comprising sliding the carrier axially along the outer perimeter of receptacle until the carrier meets a stop.

12. The method of claim 10, wherein the transfer top is connected to an inserter.

13. The method of claim 10, wherein the cap is contained within an inserter.

14. The method of claim 10, wherein the cap is connected to an inserter.

15. The method of claim 10, further comprising the step of connecting the cap to an inserter.

16. The method of claim 10, comprising the step of transferring the cap from the carrier to an inserter.

17. The method of claim 10, wherein the carrier is ring-shaped and the receptacle is cylindrical.

18. The method of claim 10, wherein the carrier is shaped to match the receptacle shape.

19. A method for transferring semen from a device, the method comprising:

lowering the closed, distal end of a condom containing a semen ejaculate deposit into a receptacle;

everting the open, proximal end of the condom over an outer perimeter of the receptacle;

placing a transfer top defining a passage atop the receptacle; and moving a piston relative to the receptacle and transferring the semen deposit ejaculate from the closed distal end of the condom through the passage in the transfer top which the semen deposit passes through to exit the device, wherein the receptacle is effectively sealed from air passage by the piston at the bottom end and by a mating surface between the receptacle and the transfer top at the top end; and wherein the open, proximal end of the condom is moved axially along the outer perimeter of the receptacle after the condom is everted until the closed, distal end of the condom is raised upward towards the top of the receptacle before placing the transfer top.

20. The method of claim 19 further comprising a cervical cap is separably attached to a transfer top.

21. The method of claim 20, wherein the transfer top is separably connected to an inserter.

22. The method of claim 21, wherein the cervical cap is contained within an inserter.

23. The method of claim 21, wherein the cervical cap is separably connected to an inserter.

24. The method of claim 20, comprising the step of connecting the cervical cap to an inserter.

25. The method of claim 20, comprising the step of transferring the cervical cap from the transfer top to an inserter.

26. The method of claim 20 further comprising:

a removal string attached to the cervical cap disposed in contact with a cervix, the string is of sufficient length to protrude from the person's vagina; and the method further comprises inserting the cervical cap into a person's vagina with a portion of the removal string protruding from the vagina.

27. The method of claim 26 wherein the string has two ends and both ends are attached to the cervical cap.

28. The method of claim 26 wherein the portion of the removal string protruding from the vagina is formed into a loop.

29. The method of claim 26 wherein the portion of the removal string protruding from the vagina is affixed to a pull tab.

30. The method of claim 19, wherein the device comprises inverting the receptacle piston and transfer top and the receptacle and piston, before transferring the semen deposit through the passage in the transfer top.

31. The method of claim 19, further comprising placing the transfer top on the receptacle for protected storage of the semen deposit.

32. The method of claim 19, further comprising placing a cover on the receptacle for protected storage of the semen deposit.

* * * * *